| United States Patent [19] | [11] Patent Number: 4,654,421 |
|---|---|
| Tanaka et al. | [45] Date of Patent: Mar. 31, 1987 |

[54] 4-SUBSTITUTED PHENYL CROTYL ETHER DERIVATIVE

[75] Inventors: Yasuyuki Tanaka; Haruyoshi Takatsu; Kiyohumi Takeuchi, all of Tokyo, Japan

[73] Assignee: Dainippon Ink and Chemicals, Inc., Tokyo, Japan

[21] Appl. No.: 874,930

[22] Filed: Jun. 16, 1986

[30] Foreign Application Priority Data

Jun. 20, 1985 [JP] Japan .................................. 60-134476
Sep. 11, 1985 [JP] Japan .................................. 60-200833

[51] Int. Cl.$^4$ .................... C07C 43/215; C07D 239/04
[52] U.S. Cl. ..................................... 544/335; 568/631; 568/642; 252/299.61; 252/299.63
[58] Field of Search ................. 568/642, 631; 544/335

[56] References Cited

U.S. PATENT DOCUMENTS

| 4,368,135 | 1/1983 | Osman | 568/642 X |
|---|---|---|---|
| 4,422,951 | 12/1983 | Sugimori et al. | 568/631 X |
| 4,477,369 | 10/1984 | Sugimori et al. | 568/642 X |
| 4,545,922 | 10/1985 | Eidenschink et al. | 568/642 X |
| 4,551,264 | 11/1985 | Eidenschink et al. | 568/631 X |

*Primary Examiner*—Bernard Helfin
*Attorney, Agent, or Firm*—Armstrong, Nikaido, Marmelstein & Kubovcik

[57] ABSTRACT

4-Substituted phenyl crotyl ether derivative is disclosed, which is a novel nematic liquid crystal compound having a comparatively high N-I point and which, when preparing a practically usable mixed liquid crystal having an N-I point higher than 65° C. by mixing this compound with at least one other liquid crystal compound, can minimize the increase range of the viscosity of the resulting mixed liquid crystal.

1 Claim, 1 Drawing Figure

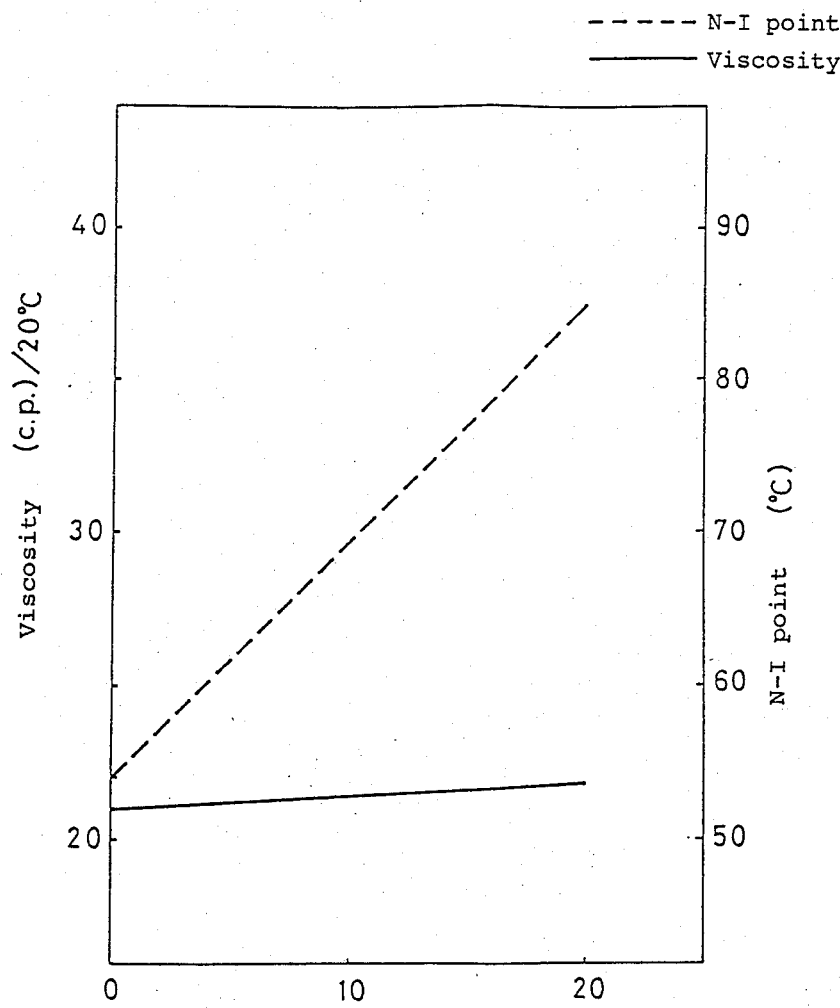

4-SUBSTITUTED PHENYL CROTYL ETHER DERIVATIVE

FIELD OF THE INVENTION

This invention relates to a 4-substituted phenyl crotyl ether derivative which is a novel nematic liquid crystal compound useful as an electrooptical display material.

BACKGROUND OF THE INVENTION

Representative examples of liquid crystal display cells are a field effect mode cell proposed by M. Schadt et al., *APPLIED PHYSICS LETTERS,* 18, 127–128 (1971), a dynamic scattering mode cell proposed by G. H. Heilmeier et al., *PROCEEDING OF THE I.E.E.E.,* 56, 1162–1171 (1968), a guest-host mode cell proposed by G. H. Heilmeier, *APPLIED PHYSICS LETTERS,* 13, 91 (1968) and E. L. White et al., *JOURNAL OF APPLIED PHYSICS,* 45, 4718 (1974).

Of those liquid crystal cells, the field effect mode cell is particularly excellent and is widely used. The field effect mode cell requires various characteristics, and a quick response time and a sharp transmittance-voltage are the important characteristics required in order to produce highly multiplexed TN-LCD. It is known that a compound having a low viscosity represented by

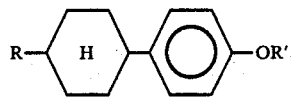

(hereinafter referred to as "Compound (a)" for simplicity) is useful as a nematic liquid crystal material for quick response time and a compound having a small $K_{33}/K_{11}$ value (ratio of elastic constants of bent to spray) represented by

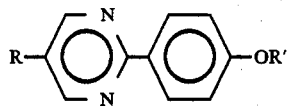

(hereinafter referred to as "Compound (b)" for simplicity) is useful as a nematic liquid crystal material having a sharp transmittance-voltage characteristics. The excellent characteristics of those compounds, i.e., low viscosity and small $K_{33}/K_{11}$ value, are mainly due to the skeletons

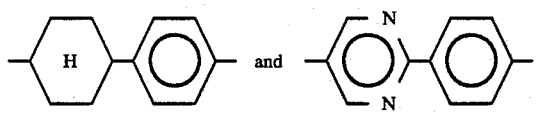

of respective compound.

In general, the liquid crystal material used in liquid crystal display cells must have various characteristics, and it is the important characteristic for all display cells to have a nematic phase over a wide temperature range including room temperature. Many liquid crystal cells practically used having such characteristics are generally prepared by mixing at least one compound having the nematic phase in the vicinity of room temperature and at least one compound having the nematic phase at a temperature region higher than room temperature. Many of mixed liquid crystals practically used, for example, in the production of TN-LCD must have the nematic phase over a temperature range of from $-30°$ C. to $65°$ C.

Therefore, a liquid crystal compound containing Compound (a) having excellent quick response time or Compound (b) having sharp transmittance-voltage characteristic is used in combination with a liquid crystal compound having three rings which has a high nematic phase-isotropic liquid phase transition point (hereinafter referred to as "N-I point" for simplicity) in order to elevate the N-I point of the mixed liquid crystal. The N-I point is elevated by mixing such compound having three rings, but excellent characteristics Compound (a) or Compound (b) inherently has tend to be deteriorated. Therefore, compounds having a high N-I point are demanded.

Further, in order to satisfy the requirement that the mixed crystal liquid must have the nematic phase over the temperature of from $-30°$ C. to $65°$ C., a compound having a crystal phase-nematic phase transition point (hereinafter referred to as "C-N point" for simplicity) of about $100°$ C. and the N-I point of about $200°$ C., such as 4,4'-substituted terphenyl, 4,4'-substituted biphenylcyclohexane, or 4,4'-substituted benzoyloxybenzoic acid phenyl ester, is occasionally used as the compound having the nematic phase in the temperature range higher than room temperature.

However, in the case where those compounds are mixed in amounts sufficient to make the N-I point of the mixed liquid crystal at $65°$ C. or more, the compounds exhibit undesirable properties to increase the viscosity of the mixed liquid crystal obtained, thereby decreasing the response time.

SUMMARY OF THE INVENTION

Accordingly, one object of this invention is to provide a nematic liquid crystal compound having a comparatively high N-I point.

Another object of this invention is to provide a nematic liquid crystal compound having excellent quick response time and sharp transmittance-voltage characteristic and also having a comparatively high N-I point.

Further object of this invention is to provide a liquid crystal compound which, when preparing a practically usable mixed liquid crystal having an N-I point of $65°$ C. or more by mixing at least one other liquid crystal compound, can minimize the increase range of the viscosity of the mixed liquid crystal.

The nematic liquid crystal compound according to this invention is 4-substituted crotyl phenyl derivative represented by the formula

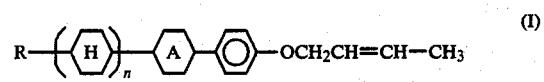

(I)

wherein R represents a straight chain alkyl group having 1 to 9 carbon atoms,

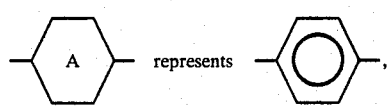

 or 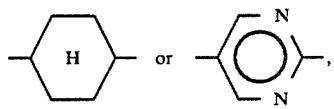

and n represents 0, 1 or 2, and wherein

is a trans-configuration (equatorial-equatorial), and crotyl group is a trans-configuration.

BRIEF DESCRIPTION OF THE DRAWING

FIGURE is a graph showing the relationship between the N-I point of the mixed liquid crystal obtained by adding Compound No. 2 which is one of the compounds of this invention to the host liquid crystal (A) which is commercially available and the amount of Compound No. 4 added, and also the relationship between the viscosity of the mixed liquid crystal and the amount of Compound No. 4 added.

DETAILED DESCRIPTION OF THE INVENTION

The compound of formula (I) according to this invention can be prepared by the following procedures, wherein R,

and n in the following formula (II) have the same meaning as in R,

and n in the formula (I) above, respectively.

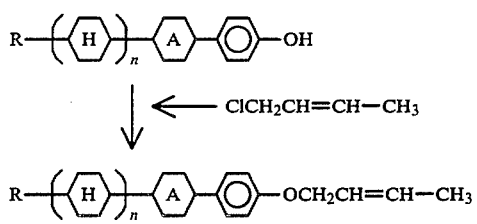

A compound of the formula (II) is reacted with an alkali such as potassium hydroxide in an organic solvent such as ethanol to obtain a phenolate and a crotyl halide such as trans-crotyl chloride is reacted with the phenolate to prepare a compound of formula (I) according to this invention.

The transition points of the representative compounds of the formula (I) prepared above are shown in Table 1 below.

TABLE 1

R―(H)ₙ―A―⌬―OCH₂CH=CH―CH₃

| Compound No. | n | R | A | Transition Temperature |
|---|---|---|---|---|
| 1 | 0 | n-C₃H₇— | H (cyclohexane) | 43° C. (C → N) 58° C. (N ⇌ I) |
| 2 | 0 | n-C₆H₁₃— | pyrimidine (N,N) | 54° C. (C → N) 61° C. (N ⇌ I) |
| 3 | 1 | n-C₃H₇— | phenyl | 128° C. (C → S) 175° C. (S ⇌ N) 212° C. (N ⇌ I) |
| 4 | 1 | n-C₃H₇— | H (cyclohexane) | 70° C. (C → S) 150° C. (S ⇌ N) 210° C. (N ⇌ I) |
| 5 | 2 | n-C₃H₇— | phenyl | Decomposed at 220° C. in the form of crystal |

C: Crystal phase
S: Smectic phase
N: Nematic phase
I: Isotropic liquid

As can be seen from the data shown in Table 1 above, Compound No. 1 has the N-I point of 58° C. which is 26° C. higher than the N-I point (32° C.) of the corresponding compound of formula

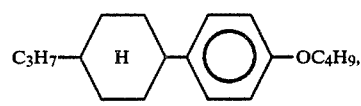

and Compound No. 2 has the N-I point of 61° C. which is 8° C. higher than the N-I point (53° C.) of the corresponding compound of the formula

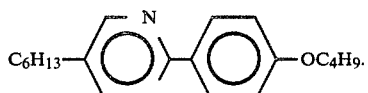

Thus, Compound Nos. 1 and 2 according to this invention have the N-I point higher than that of the conentional nematic liquid crystal compound (R—[A]—〇—OR')

having excellent characteristics.

Further, the compound of formula (I) according to this invention is a nematic liquid crystal compound having weakly negative dielectric constant anisotropy, and therefore, can be used as a material for a dynamic scattering mode display cell in the form of mixture with other nematic liquid crystal compound having negative or weakly positive dielectric constant anisotropy, and can also be used as a material of a field effect mode display cell in the form of mixture with other nematic liquid crystal compound having strongly positive dielectric constant anisotropy.

Examples of the compound which can be used in combination with the compounds of the formula (I) above include 4-substituted phenyl 4'-substituted benzoate, 4-substituted phenyl 4'-substituted cyclohexanecarboxylate, 4-substituted biphenyl 4'-substituted cyclohexanecarboxylate, 4-substituted phenyl 4'-(4''-substituted cyclohexanecarbonyloxy)benzoate, 4-substituted phenyl 4'-(4''-substituted cyclohexyl)-benzoate, 4-substituted cyclohexyl 4'-(4''-substituted cyclohexyl)-benzoate, 4-substituted 4'-substituted biphenyl, 4-substituted phenyl 4'-substituted cyclohexane, 4-substituted 4'-substituted terphenyl, 4-substituted biphenyl 4'-substituted cyclohexane and 2-(4'-substituted phenyl)-5-substituted pyrimidine.

Table 2 below shows the N-I point and the viscosity determined with respect to a mixed liquid crystal comprising 80 wt% of a matrix liquid crystal (A) now in widespread use as a nematic liquid crystal material having an excellent time sharing driving characteristic and 20 wt% of Compound No. 4 of the formula (I) shown in Table 1. For the sake of comparison, the N-I point and the viscosity determined with respect to the host liquid crystal (A) itself are also shown in Table 2 below.

The matrix liquid crystal comprises n-C$_3$H$_7$—[H]—〇—CN    20 wt % n-C$_5$H$_{11}$—[H]—〇—CN    16 wt %

-continued n-C$_7$H$_{15}$—[H]—〇—CN    16 wt % n-C$_3$H$_7$—[H]—COO—〇—O—C$_2$H$_5$    8 wt % n-C$_3$H$_7$—[H]—COO—〇—O—n-C$_4$H$_9$    8 wt % n-C$_4$H$_9$—[H]—COO—〇—OCH$_3$    8 wt % n-C$_4$H$_9$—[H]—COO—〇—OC$_2$H$_5$    8 wt % n-C$_5$H$_{11}$—[H]—COO—〇—OCH$_3$    8 wt % and n-C$_5$H$_{11}$—[H]—COO—〇—OC$_2$H$_5$    8 wt %

TABLE 2

| Liquid Crystal | N-I Point (°C.) | Viscosity (c.p./20° C.) |
| --- | --- | --- |
| (A) | 54.0 | 21.0 |
| (A) + No. 4 | 85.0 | 21.8 |

The relationship between the N-I point of the above described mixed liquid crystal and the amount of Compound No. 4 added and also the relationship between the viscosity of the mixed liquid crystal and the amount of Compound No. 2 added are shown in the attached FIGURE. It can be understood from the FIGURE that the compound of formula (I) can raise the N-I point of the matrix liquid crystal to a practically satisfactory extent, and increase of the viscosity is slight.

Table 3 below shows the N-I point of Compound No. 4 of formula (I) according to this invention and the N-I point of the conventional compound similar to Compound No. 4 of formula (I) according to this invention.

TABLE 3

| Compound | Structural Formula | N-I Point (° C.) |
| --- | --- | --- |
| Compound No. 4 | n-C$_3$H$_7$—[H]—[H]—〇—OCH$_2$CH=CH—CH$_3$ | 210 |

TABLE 3-continued

| Compound | Structural Formula | N-I Point (° C.) |
|---|---|---|
| Conventional Compound* | 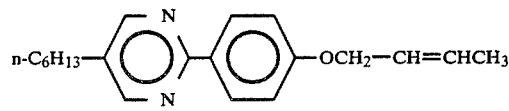 | 190 |

*Japanese Patent Application (OPI) No. 165328/82
(The term "OPI" as used herein means an "unexamined published application")

As can be understood also from the above comparison, the compound of formula (I) according to this invention is a liquid crystal compound having the N-I point higher than that of the conventional compound which has the same molecular skeleton as the compound according to this invention.

This invention will be now explained in greater detail by reference to the following examples, but the invention is not to be construed as being limited thereto. Unless otherwise indicated, all percents, parts, ratios and the like are by weight.

EXAMPLE 1

4.7 g (0.022 mol) of a compound represented by the formula

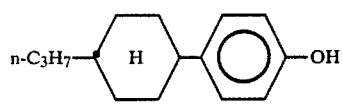

was dissolved in 33 ml of ethanol, and 1.5 g (0.023 mol) of 85% potassium hydroxide was added thereto. 2.2 g (0.024 mol) of transcrotyl chloride was dropwise added to the resulting mixture at reflux temperature while stirring the mixture, and the reaction was further conducted at the same temperature for 5 hours. After cooling, water was added to the reaction mixture, the reaction product was extracted with diethyl ether, and after the extract solution was washed with water and dried, the ether was distilled off from the solution.

The reaction product thus obtained was purified by recrystallizing from ethanol to obtain 4.5 g (0.0017 mol) of the following compound.

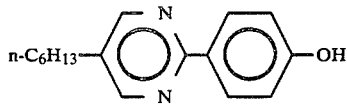

Yield: 77%, Transition point: 43° C. (C→N); 58° C. (N⇌I).

EXAMPLE 2

10.0 g (0.0391 mol) of a compound represented by the formula

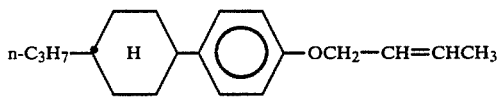

was dissolved in 70 ml of ethanol, and 2.8 g (0.043 mol) of 85% potassium hydroxide was added thereto. 3.9 g (0.043 mol) of transcrotyl chloride was dropwise added to the resulting mixture at reflux temperature while stirring the mixture, and the reaction was conducted at the same temperature for 5 hours. After cooling, water was added to the reaction mixture, the reaction product was extracted with diethyl ether, and after the extract solution was washed with water and dried, the ether was distilled off from the solution.

The reaction product thus obtained was purified by recrystallizing from ethanol to obtain 9.4 g (0.030 mol) of the following compound.

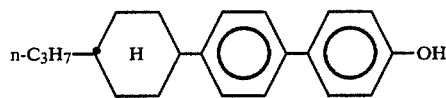

Yield: 77%, Transition temperature: 54° C. (C→N); 61° C. (N⇌I).

EXAMPLE 3

4.3 g (0.015 mol) of a compound having the formula

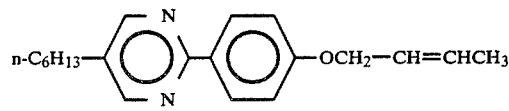

was dissolved in 34 ml of ethanol, and 1.1 g (0.017 mol) of 85% potassium hydroxide was added thereto. 1.5 g (0.017 mol) of transcrotyl chloride was dropwise added to the resulting mixture at reflux temperature while stirring, and the reaction was conducted at the same temperature for 5 hours. After cooling, water was added to the reaction mixture, the reaction product was extracted with toluene, and after the extract solution was washed with water and dried, toluene was distilled off from the solution.

The reaction product thus obtained was purified by recrystallizing from ethyl acetate to obtain 3.3 g (0.0095 mol) of the following compound.

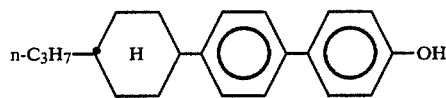

Yield: 63%, Transition temperature: 128° C. (C→S); 175° C. (S⇌N); 212° C. (N⇌I).

EXAMPLE 4

The following compound was obtained in the same manner as in Example 3 except that

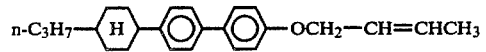 OH was used in place of

-continued

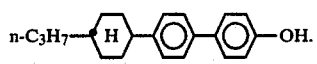

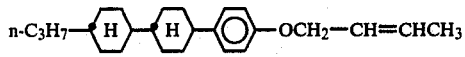

Yield: 70%, Transition temperature: 128° C. (C→S); 175° C. (S⇌N); 212° C. (N⇌I).

The compound of the formula (I) according to this invention is a liquid crystal compound having an N-I transition point higher than that of the conventional liquid crystal compound having

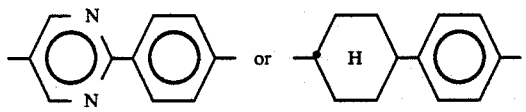

skeleton, and is a compound having a sharp transmittance-voltage characteristic due to the presence of

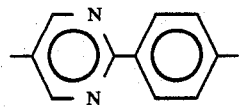

skeleton and an excellent quick response time due to the presence of

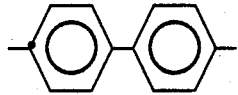

skeleton.

Further, the compound according to this invention is a liquid crystal compound which, when preparing a practically usable mixed liquid crystal having an N-I point of 65° C. or more by mixing at least one other liquid crystal compound, can minimize the increase range of the viscosity of the resulting mixed liquid crystal.

While the invention has been described in detail and with reference to specific embodiments thereof, it will be apparent to one skilled in the art that various changes and modifications can be made therein without departing from the spirit and scope thereof.

What is claimed is:

1. A compound represented by the formula

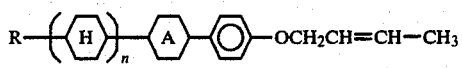

wherein R represents a straight chain alkyl group having 1 to 9 carbon atoms,

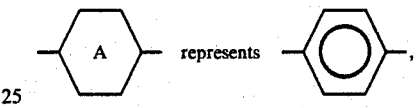

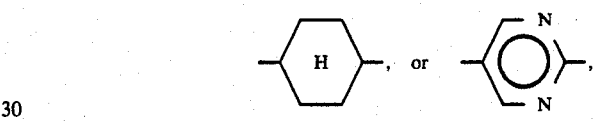

and n represents 0, 1 or 2, and wherein

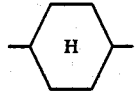

is a trans-configuration (equatorial-equatorial), and crotyl group is a trans-configuration.

* * * * *

Notice of Adverse Decisions in Interference

In Interference No. 102,313, involving Patent No. 4,654,421, Y. Tanaka, H. Takatsu, K. Takeuchi, 4-SUBSTITUTED PHENYL CROTYL ETHER DERIVITIVE, final judgement adverse to the patentees was rendered Aug. 3, 1990, as to claim 1.

[*Official Gazette October 23, 1990*]